United States Patent
Boyle et al.

(10) Patent No.: US 7,662,166 B2
(45) Date of Patent: *Feb. 16, 2010

(54) SHEATHLESS EMBOLIC PROTECTION SYSTEM

(75) Inventors: William J. Boyle, Fallbrook, CA (US); Richard S. Stack, Chapel Hill, NC (US)

(73) Assignee: Advanced Cardiocascular Systems, Inc., Santa Clara, CA (US)

( * ) Notice: Subject to any disclaimer, the term of this patent is extended or adjusted under 35 U.S.C. 154(b) by 584 days.

This patent is subject to a terminal disclaimer.

(21) Appl. No.: 11/352,713

(22) Filed: Feb. 13, 2006

(65) Prior Publication Data

US 2006/0129183 A1 Jun. 15, 2006

Related U.S. Application Data

(63) Continuation of application No. 09/945,152, filed on Aug. 31, 2001, now Pat. No. 7,018,393, which is a continuation-in-part of application No. 09/740,560, filed on Dec. 19, 2000, now Pat. No. 6,506,203.

(51) Int. Cl.
 *A61M 29/00* (2006.01)
(52) U.S. Cl. .................................................... 606/200
(58) Field of Classification Search ................. 606/200; 604/104, 105, 106, 107, 108
See application file for complete search history.

(56) References Cited

U.S. PATENT DOCUMENTS

| | | | |
|---|---|---|---|
| 3,952,747 A | 4/1976 | Kimmell, Jr. | |
| 4,425,908 A | 1/1984 | Simon | |
| 4,494,531 A | 1/1985 | Gianturco | |
| 4,612,931 A | 9/1986 | Dormia | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,662,885 A | 5/1987 | DiPisa, Jr. | |
| 4,688,553 A | 8/1987 | Metals | |
| 4,706,671 A | 11/1987 | Weinrib | |
| 4,723,549 A | 2/1988 | Wholey et al. | |

(Continued)

FOREIGN PATENT DOCUMENTS

EP 0427429 A3 9/1991

(Continued)

OTHER PUBLICATIONS

Dilitation of the Carotid Artery By A Temporary Carotid Filter By A. Beck, St. Milic, A.M. Spagnoli, Nov.-Dec. Issue of OPLITAI, An International Journal on Military Medicine and Health Emergencies, pp. 67-74.

*Primary Examiner*—Todd E Manahan
*Assistant Examiner*—Jonathan A Hollm
(74) *Attorney, Agent, or Firm*—Fulwider Patton LLP

(57) ABSTRACT

A system for enabling the insertion and removal of an embolic protection device, for capturing and retaining embolic debris which may be created during the performance of a therapeutic interventional procedure in a stenosed or occluded region of a blood vessel. The system, in an embodiment thereof, enables the device to be compressed for insertion thereof through a patient's vasculature so as to cross the stenosis in a low profile, and to enable release of compression thereof for expansion and deployment of the device at a location distal to the interventional procedure site.

21 Claims, 5 Drawing Sheets

U.S. PATENT DOCUMENTS

| | | | |
|---|---|---|---|
| 4,727,873 A | 3/1988 | Mobin-Uddin | |
| 4,781,177 A | 11/1988 | Lebigot | |
| 4,790,812 A | 12/1988 | Hawkins, Jr. et al. | |
| 4,790,813 A | 12/1988 | Kensey | |
| 4,794,928 A | 1/1989 | Kletschka | |
| 4,832,055 A | 5/1989 | Palestrant | |
| 4,873,978 A | 10/1989 | Ginsburg | |
| 4,921,478 A | 5/1990 | Solano et al. | |
| 4,921,484 A | 5/1990 | Hillstead | |
| 4,969,891 A | 11/1990 | Gewertz | |
| 4,990,156 A | 2/1991 | Lefebvre | |
| 4,997,435 A | 3/1991 | Demeter | |
| 4,998,539 A | 3/1991 | Delsanti | |
| 5,053,008 A | 10/1991 | Bajaj | |
| 5,064,428 A | 11/1991 | Cope et al. | |
| 5,071,407 A | 12/1991 | Termin et al. | |
| 5,092,839 A | 3/1992 | Kipperman | |
| 5,100,423 A | 3/1992 | Fearnot | |
| 5,100,425 A | 3/1992 | Fischell et al. | |
| 5,102,415 A | 4/1992 | Guenther et al. | |
| 5,108,419 A | 4/1992 | Reger et al. | |
| 5,152,777 A | 10/1992 | Goldberg et al. | |
| 5,158,548 A | 10/1992 | Lau et al. | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,383,887 A | 1/1995 | Nadal | |
| 5,421,832 A | 6/1995 | Lefebvre | |
| 5,437,632 A | 8/1995 | Engelson | |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,549,626 A | 8/1996 | Miller et al. | |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,658,296 A | 8/1997 | Bates et al. | |
| 5,662,671 A | 9/1997 | Barbut et al. | |
| 5,669,933 A | 9/1997 | Simon et al. | |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,746,767 A | 5/1998 | Smith | |
| 5,755,790 A | 5/1998 | Chevillon et al. | |
| 5,769,816 A | 6/1998 | Barbut et al. | |
| 5,772,674 A | 6/1998 | Nakhjavan | |
| 5,776,162 A | 7/1998 | Kleshinski | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maas | |
| 5,848,964 A | 12/1998 | Samuels | |
| 5,868,708 A | 2/1999 | Hart et al. | |
| 5,876,367 A | 3/1999 | Kaganov et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,935,139 A | 8/1999 | Bates | |
| 5,941,869 A | 8/1999 | Patterson et al. | |
| 5,941,896 A | 8/1999 | Kerr | |
| 5,944,728 A | 8/1999 | Bates | |
| 5,954,745 A | 9/1999 | Gertler et al. | |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,013,093 A | 1/2000 | Nott et al. | |
| 6,022,336 A | 2/2000 | Zadno-Azizi et al. | |
| 6,027,520 A | 2/2000 | Tsugita et al. | |
| 6,042,598 A | 3/2000 | Tsugita et al. | |
| 6,051,015 A | 4/2000 | Maahs | |
| 6,053,932 A | 4/2000 | Daniel et al. | |
| 6,059,814 A | 5/2000 | Ladd | |
| 6,066,158 A | 5/2000 | Engelson et al. | |
| 6,074,357 A | 6/2000 | Kaganov et al. | |
| 6,086,605 A | 7/2000 | Barbut et al. | |
| 6,090,097 A | 7/2000 | Barbut et al. | |
| 6,096,053 A | 8/2000 | Bates | |
| 6,099,534 A | 8/2000 | Bates et al. | |
| 6,099,549 A | 8/2000 | Bosma et al. | |
| 6,117,154 A | 9/2000 | Barbut et al. | |
| 6,129,739 A | 10/2000 | Khosravi | |
| 6,136,015 A | 10/2000 | Kurz | |
| 6,136,016 A | 10/2000 | Barbut et al. | |
| 6,142,987 A | 11/2000 | Tsugita | |
| 6,152,946 A * | 11/2000 | Broome et al. ............... 606/200 |
| 6,152,947 A | 11/2000 | Ambrisco et al. | |
| 6,165,198 A | 12/2000 | McGurk et al. | |
| 6,165,200 A | 12/2000 | Tsugita et al. | |
| 6,168,579 B1 | 1/2001 | Tsugita et al. | |
| 6,168,604 B1 | 1/2001 | Cano | |
| 6,171,327 B1 | 1/2001 | Daniel et al. | |
| 6,171,328 B1 | 1/2001 | Addis | |
| 6,174,318 B1 | 1/2001 | Bates et al. | |
| 6,176,849 B1 | 1/2001 | Yang et al. | |
| 6,179,859 B1 | 1/2001 | Bates et al. | |
| 6,179,860 B1 | 1/2001 | Fulton, III et al. | |
| 6,179,861 B1 | 1/2001 | Khosravi et al. | |
| 6,187,025 B1 | 2/2001 | Machek | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,224,620 B1 | 5/2001 | Maahs | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,241,746 B1 | 6/2001 | Bosma et al. | |
| 6,245,012 B1 | 6/2001 | Kleshinski | |
| 6,245,087 B1 | 6/2001 | Addis | |
| 6,245,088 B1 | 6/2001 | Lowery | |
| 6,245,089 B1 | 6/2001 | Daniel et al. | |
| 6,251,122 B1 | 6/2001 | Tsukernik | |
| 6,254,633 B1 | 7/2001 | Pinchuk et al. | |
| 6,258,115 B1 | 7/2001 | Dubrul | |
| 6,258,120 B1 | 7/2001 | McKenzie et al. | |
| 6,264,663 B1 | 7/2001 | Cano | |
| 6,264,672 B1 | 7/2001 | Fisher | |
| 6,267,776 B1 | 7/2001 | O'Connell | |
| 6,267,777 B1 | 7/2001 | Bosma et al. | |
| 6,270,477 B1 | 8/2001 | Bagaosian | |
| 6,270,513 B1 | 8/2001 | Tsugita et al. | |
| 6,273,901 B1 | 8/2001 | Whitcher et al. | |
| 6,277,138 B1 | 8/2001 | Levinson et al. | |

| Patent | Kind | Date | Inventor |
|---|---|---|---|
| 6,277,139 | B1 | 8/2001 | Levinson et al. |
| 6,280,451 | B1 | 8/2001 | Bates et al. |
| 6,287,321 | B1 | 9/2001 | Jang |
| 6,290,656 | B1 | 9/2001 | Boyle et al. |
| 6,290,710 | B1 | 9/2001 | Cryer et al. |
| 6,295,989 | B1 | 10/2001 | Connors, III |
| 6,306,163 | B1 | 10/2001 | Fitz |
| 6,319,242 | B1 | 11/2001 | Patterson et al. |
| 6,319,268 | B1 | 11/2001 | Ambrisco et al. |
| 6,325,815 | B1 | 12/2001 | Kusleika et al. |
| 6,336,934 | B1 | 1/2002 | Gilson et al. |
| 6,340,364 | B2 | 1/2002 | Kanesaka |
| 6,340,465 | B1 | 1/2002 | Hsu et al. |
| 6,346,116 | B1 | 2/2002 | Brooks et al. |
| 6,348,056 | B1 | 2/2002 | Bates et al. |
| 6,355,051 | B1 | 3/2002 | Sisskind et al. |
| 6,361,545 | B1 | 3/2002 | Macoviak et al. |
| 6,361,546 | B1 | 3/2002 | Khosravi |
| 6,364,895 | B1 | 4/2002 | Greenhalgh |
| 6,364,896 | B1 | 4/2002 | Addis |
| 6,371,969 | B1 | 4/2002 | Tsugita et al. |
| 6,371,970 | B1 | 4/2002 | Khosravi et al. |
| 6,371,971 | B1 * | 4/2002 | Tsugita et al. ............ 606/200 |
| 6,375,670 | B1 | 4/2002 | Greenhalgh |
| 6,383,206 | B1 | 5/2002 | Gillick et al. |
| 6,384,062 | B1 | 5/2002 | Ikeda et al. |
| 6,391,044 | B1 | 5/2002 | Yadav et al. |
| 6,394,978 | B1 | 5/2002 | Boyle et al. |
| 6,395,014 | B1 | 5/2002 | Macoviak et al. |
| 6,398,756 | B2 | 6/2002 | Peterson et al. |
| 6,402,771 | B1 | 6/2002 | Palmer et al. |
| 6,406,471 | B1 | 6/2002 | Jang et al. |
| 6,423,032 | B2 | 7/2002 | Parodi |
| 6,423,086 | B1 | 7/2002 | Barbut et al. |
| 6,425,909 | B1 | 7/2002 | Dieck et al. |
| 6,428,559 | B1 | 8/2002 | Johnson |
| 6,432,122 | B1 | 8/2002 | Gilson et al. |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma |
| 6,443,979 | B1 | 9/2002 | Stalker et al. |
| 6,447,530 | B1 | 9/2002 | Ostrovsky et al. |
| 6,447,531 | B1 | 9/2002 | Amplatz |
| 6,450,989 | B2 | 9/2002 | Dubrul et al. |
| 6,458,139 | B1 | 10/2002 | Palmer et al. |
| 6,461,370 | B1 | 10/2002 | Gray et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,497 | B2 | 11/2002 | Wensel et al. |
| 6,485,500 | B1 | 11/2002 | Kokish et al. |
| 6,485,501 | B1 | 11/2002 | Green |
| 6,485,502 | B2 | 11/2002 | Don Michael et al. |
| 6,485,507 | B1 | 11/2002 | Walak et al. |
| 6,494,895 | B2 | 12/2002 | Addis |
| 6,499,487 | B1 | 12/2002 | McKenzie et al. |
| 6,500,166 | B1 | 12/2002 | Azizi et al. |
| 6,506,203 | B1 | 1/2003 | Boyle et al. |
| 6,506,205 | B2 | 1/2003 | Goldberg et al. |
| 6,511,492 | B1 | 1/2003 | Rosenbluth |
| 6,511,496 | B1 | 1/2003 | Huter et al. |
| 6,511,497 | B1 * | 1/2003 | Braun et al. ............ 606/200 |
| 6,511,503 | B1 | 1/2003 | Burkett et al. |
| 6,514,273 | B1 | 2/2003 | Voss et al. |
| 6,517,550 | B1 | 2/2003 | Konya et al. |
| 6,517,559 | B1 | 2/2003 | O'Connell |
| 6,520,978 | B1 | 2/2003 | Blackledge et al. |
| 6,527,746 | B1 | 3/2003 | Oslund et al. |
| 6,527,791 | B2 | 3/2003 | Fisher |
| 6,530,939 | B1 | 3/2003 | Hopkins et al. |
| 6,530,940 | B2 | 3/2003 | Fisher |
| 6,533,800 | B1 | 3/2003 | Barbut |
| 6,537,294 | B1 | 3/2003 | Boyle et al. |
| 6,537,295 | B1 | 3/2003 | Petersen |
| 6,537,296 | B2 | 3/2003 | Levinson et al. |
| 6,537,297 | B2 | 3/2003 | Tsugita et al. |
| 6,540,722 | B1 | 4/2003 | Boyle et al. |
| 6,540,767 | B1 | 4/2003 | Walak et al. |
| 6,540,768 | B1 | 4/2003 | Diaz et al. |
| 6,544,276 | B1 | 4/2003 | Azizi |
| 6,544,279 | B1 | 4/2003 | Hopkins et al. |
| 6,544,280 | B1 | 4/2003 | Daniel et al. |
| 6,547,759 | B1 | 4/2003 | Fisher |
| 6,551,268 | B1 | 4/2003 | Kaganov et al. |
| 6,551,341 | B2 | 4/2003 | Boylan et al. |
| 6,551,342 | B1 | 4/2003 | Shen et al. |
| 6,558,401 | B1 | 5/2003 | Azizi |
| 6,558,405 | B1 | 5/2003 | McInnes |
| 6,562,058 | B2 | 5/2003 | Seguin |
| 6,565,591 | B2 | 5/2003 | Kelly et al. |
| 6,569,184 | B2 | 5/2003 | Huter |
| 6,575,995 | B1 | 6/2003 | Huter et al. |
| 6,575,996 | B1 | 6/2003 | Denison et al. |
| 6,575,997 | B1 | 6/2003 | Palmer et al. |
| 6,582,447 | B1 | 6/2003 | Patel et al. |
| 6,582,448 | B1 | 6/2003 | Boyle et al. |
| 6,585,756 | B1 | 7/2003 | Strecker |
| 6,589,263 | B1 | 7/2003 | Hopkins et al. |
| 6,589,265 | B1 | 7/2003 | Palmer et al. |
| 6,592,546 | B1 | 7/2003 | Barbut et al. |
| 6,592,606 | B2 | 7/2003 | Huter et al. |
| 6,592,607 | B1 | 7/2003 | Palmer et al. |
| 6,592,616 | B1 | 7/2003 | Stack et al. |
| 6,596,011 | B2 | 7/2003 | Johnson et al. |
| 6,599,307 | B1 | 7/2003 | Huter et al. |
| 6,599,308 | B2 | 7/2003 | Amplatz |
| 6,602,269 | B2 | 8/2003 | Wallace et al. |
| 6,602,271 | B2 | 8/2003 | Adams et al. |
| 6,602,272 | B2 | 8/2003 | Boylan et al. |
| 6,602,273 | B2 | 8/2003 | Marshaii |
| 6,605,102 | B1 | 8/2003 | Mazzocchi et al. |
| 6,605,111 | B2 | 8/2003 | Bose et al. |
| 6,607,506 | B2 | 8/2003 | Kletschka |
| 6,610,077 | B1 | 8/2003 | Hancock et al. |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,682 | B2 | 9/2003 | Joergensen et al. |
| 6,620,148 | B1 | 9/2003 | Tsugita et al. |
| 6,620,182 | B1 | 9/2003 | Khosravi |
| 6,623,450 | B1 | 9/2003 | Dutta |
| 6,629,953 | B1 | 10/2003 | Boyd |
| 6,632,236 | B2 | 10/2003 | Hogendijk |
| 6,632,241 | B1 | 10/2003 | Hancock et al. |
| 6,635,068 | B1 | 10/2003 | Dubrul et al. |
| 6,635,070 | B2 | 10/2003 | Leeflang et al. |
| 6,638,293 | B1 | 10/2003 | Makowner et al. |
| 6,638,294 | B1 | 10/2003 | Palmer |
| 6,645,220 | B1 | 11/2003 | Huter et al. |
| 6,645,221 | B1 | 11/2003 | Richter |
| 6,645,223 | B2 | 11/2003 | Boyle et al. |
| 6,645,224 | B2 | 11/2003 | Gilson et al. |
| 6,652,480 | B1 | 11/2003 | Imran et al. |
| 6,652,505 | B1 | 11/2003 | Tsugita et al. |
| 6,652,554 | B1 | 11/2003 | Wholey et al. |
| 6,652,557 | B1 | 11/2003 | MacDonald |
| 6,656,202 | B2 | 12/2003 | Papp et al. |
| 6,656,203 | B2 | 12/2003 | Roth et al. |
| 6,656,204 | B2 | 12/2003 | Ambrisco et al. |
| 6,656,351 | B2 | 12/2003 | Boyle |
| 6,660,021 | B1 | 12/2003 | Palmer et al. |
| 6,663,650 | B2 | 12/2003 | Sepetka et al. |
| 6,663,651 | B2 | 12/2003 | Krolik et al. |
| 6,663,652 | B2 | 12/2003 | Daniel et al. |
| 6,673,090 | B2 | 1/2004 | Root et al. |

| Patent | Date | Inventor |
|---|---|---|
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boyle et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,379 B2 | 9/2006 | Gregory, Jr. et al. |
| 7,101,380 B2 | 9/2006 | Khachin et al. |
| 7,108,707 B2 | 9/2006 | Huter et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |

| | | | | | |
|---|---|---|---|---|---|
| 2002/0138094 A1 | 9/2002 | Borillo et al. | 2003/0158574 A1 | 8/2003 | Esch et al. |
| 2002/0138095 A1 | 9/2002 | Mazzocchi et al. | 2003/0163064 A1 | 8/2003 | Vrba et al. |
| 2002/0143360 A1 | 10/2002 | Douk et al. | 2003/0171770 A1 | 9/2003 | Kusleika et al. |
| 2002/0143361 A1 | 10/2002 | Douk et al. | 2003/0171771 A1 | 9/2003 | Anderson et al. |
| 2002/0151927 A1 | 10/2002 | Douk et al. | 2003/0171803 A1 | 9/2003 | Shimon |
| 2002/0156456 A1 | 10/2002 | Fisher | 2003/0176884 A1 | 9/2003 | Berrada et al. |
| 2002/0161390 A1 | 10/2002 | Mouw | 2003/0176885 A1 | 9/2003 | Broome et al. |
| 2002/0161392 A1 | 10/2002 | Dubrul | 2003/0176886 A1 | 9/2003 | Wholey et al. |
| 2002/0161393 A1 | 10/2002 | Demond et al. | 2003/0176889 A1 | 9/2003 | Boyle et al. |
| 2002/0161395 A1 | 10/2002 | Douk et al. | 2003/0181942 A1 | 9/2003 | Sutton et al. |
| 2002/0165576 A1 | 11/2002 | Boyle et al. | 2003/0181943 A1 | 9/2003 | Daniel et al. |
| 2002/0169414 A1 | 11/2002 | Kletschka | 2003/0187474 A1 | 10/2003 | Keegan et al. |
| 2002/0169458 A1 | 11/2002 | Connors, III | 2003/0187475 A1 | 10/2003 | Tsugita et al. |
| 2002/0169472 A1 | 11/2002 | Douk et al. | 2003/0187495 A1 | 10/2003 | Cully et al. |
| 2002/0169474 A1 | 11/2002 | Kusleika et al. | 2003/0191493 A1 | 10/2003 | Epstein et al. |
| 2002/0173815 A1 | 11/2002 | Hogendijk et al. | 2003/0195554 A1 | 10/2003 | Shen et al. |
| 2002/0173817 A1 | 11/2002 | Kletschka et al. | 2003/0195555 A1 | 10/2003 | Khairkhahan et al. |
| 2002/0188313 A1 | 12/2002 | Johnson et al. | 2003/0195556 A1 | 10/2003 | Stack et al. |
| 2002/0188314 A1 | 12/2002 | Anderson et al. | 2003/0199819 A1 | 10/2003 | Beck |
| 2002/0193825 A1 | 12/2002 | McGuckin et al. | 2003/0199921 A1 | 10/2003 | Palmer et al. |
| 2002/0193826 A1 | 12/2002 | McGuckin et al. | 2003/0204168 A1 | 10/2003 | Bosme et al. |
| 2002/0193827 A1 | 12/2002 | McGuckin et al. | 2003/0204202 A1 | 10/2003 | Palmer et al. |
| 2002/0193828 A1 | 12/2002 | Griffin et al. | 2003/0208222 A1 | 11/2003 | Zadno-Azizi |
| 2003/0004536 A1 | 1/2003 | Boylan et al. | 2003/0208224 A1 | 11/2003 | Broome |
| 2003/0004537 A1 | 1/2003 | Boyle et al. | 2003/0208225 A1 | 11/2003 | Goll et al. |
| 2003/0004539 A1 | 1/2003 | Linder et al. | 2003/0208226 A1 | 11/2003 | Bruckheimer et al. |
| 2003/0004540 A1 | 1/2003 | Linder et al. | 2003/0208227 A1 | 11/2003 | Thomas |
| 2003/0004541 A1 | 1/2003 | Linder et al. | 2003/0208228 A1 | 11/2003 | Gilson et al. |
| 2003/0009188 A1 | 1/2003 | Linder et al. | 2003/0208229 A1 | 11/2003 | Kletschka |
| 2003/0009189 A1 | 1/2003 | Gilson et al. | 2003/0212429 A1 | 11/2003 | Keegan et al. |
| 2003/0015206 A1 | 1/2003 | Roth et al. | 2003/0212431 A1 | 11/2003 | Brady et al. |
| 2003/0018354 A1 | 1/2003 | Roth et al. | 2003/0212434 A1 | 11/2003 | Thielen |
| 2003/0023265 A1 | 1/2003 | Forber | 2003/0216774 A1 | 11/2003 | Larson |
| 2003/0028238 A1 | 2/2003 | Burkett et al. | 2003/0220665 A1 | 11/2003 | Eskuri et al. |
| 2003/0032941 A1 | 2/2003 | Boyle et al. | 2003/0225418 A1 | 12/2003 | Eskuri et al. |
| 2003/0032977 A1 | 2/2003 | Brady et al. | 2003/0225435 A1 | 12/2003 | Huter et al. |
| 2003/0040772 A1 | 2/2003 | Hyodoh et al. | 2003/0229295 A1 | 12/2003 | Houde et al. |
| 2003/0042186 A1 | 3/2003 | Boyle et al. | 2003/0229374 A1 | 12/2003 | Brady et al. |
| 2003/0045898 A1 | 3/2003 | Harrison et al. | 2003/0233117 A1 | 12/2003 | Adams et al. |
| 2003/0057156 A1 | 3/2003 | Peterson et al. | 2003/0236545 A1 | 12/2003 | Gilson |
| 2003/0060782 A1 | 3/2003 | Bose et al. | 2004/0002730 A1 | 1/2004 | Denison et al. |
| 2003/0060843 A1 | 3/2003 | Boucher | 2004/0006361 A1 | 1/2004 | Boyle et al. |
| 2003/0060844 A1 | 3/2003 | Borillo et al. | 2004/0006364 A1 | 1/2004 | Ladd |
| 2003/0065354 A1 | 4/2003 | Boyle et al. | 2004/0006365 A1 | 1/2004 | Brady et al. |
| 2003/0069596 A1 | 4/2003 | Eskuri | 2004/0006366 A1 | 1/2004 | Huter et al. |
| 2003/0069597 A1 | 4/2003 | Petersen | 2004/0006367 A1 | 1/2004 | Johnson et al. |
| 2003/0078519 A1 | 4/2003 | Salahieh et al. | 2004/0006368 A1 | 1/2004 | Mazzocchi et al. |
| 2003/0078614 A1 | 4/2003 | Salahieh et al. | 2004/0015184 A1 | 1/2004 | Boyle et al. |
| 2003/0083692 A1 | 5/2003 | Vrba et al. | 2004/0019363 A1 | 1/2004 | Hanson et al. |
| 2003/0083693 A1 | 5/2003 | Daniel et al. | 2004/0034385 A1 | 2/2004 | Gilson et al. |
| 2003/0100917 A1 | 5/2003 | Boyle et al. | 2004/0039411 A1 | 2/2004 | Gilson et al. |
| 2003/0100918 A1 | 5/2003 | Duane | 2004/0044359 A1 | 3/2004 | Renati et al. |
| 2003/0105484 A1 | 6/2003 | Boyle et al. | 2004/0044360 A1 | 3/2004 | Lowe |
| 2003/0109824 A1 | 6/2003 | Anderson et al. | 2004/0049226 A1 | 3/2004 | Keegan et al. |
| 2003/0114879 A1 | 6/2003 | Euteneuer et al. | 2004/0059372 A1 | 3/2004 | Tsugita |
| 2003/0114880 A1 | 6/2003 | Hansen et al. | 2004/0059373 A1 | 3/2004 | Shapiro et al. |
| 2003/0120303 A1 | 6/2003 | Boyle et al. | 2004/0082967 A1 | 4/2004 | Broome et al. |
| 2003/0130680 A1 | 7/2003 | Russell | 2004/0082968 A1 | 4/2004 | Krolik et al. |
| 2003/0130681 A1 | 7/2003 | Ungs | 2004/0088000 A1 | 5/2004 | Muller |
| 2003/0130682 A1 | 7/2003 | Broome et al. | 2004/0088002 A1 | 5/2004 | Boyle et al. |
| 2003/0130684 A1 | 7/2003 | Brady et al. | 2004/0093009 A1 | 5/2004 | Denison et al. |
| 2003/0130685 A1 | 7/2003 | Daniel et al. | 2004/0093010 A1 | 5/2004 | Gesswein et al. |
| 2003/0130687 A1 | 7/2003 | Daniel et al. | 2004/0093011 A1 | 5/2004 | Vrba |
| 2003/0130688 A1 | 7/2003 | Daniel et al. | 2004/0093012 A1 | 5/2004 | Cully et al. |
| 2003/0135162 A1 | 7/2003 | Deyette, Jr. et al. | 2004/0093013 A1 | 5/2004 | Brady et al. |
| 2003/0135232 A1 | 7/2003 | Douk et al. | 2004/0098022 A1 | 5/2004 | Barone |
| 2003/0139764 A1 | 7/2003 | Levinson et al. | 2004/0098026 A1 | 5/2004 | Joergensen et al. |
| 2003/0144685 A1 | 7/2003 | Boyle et al. | 2004/0098032 A1 | 5/2004 | Papp et al. |
| 2003/0144689 A1 | 7/2003 | Brady et al. | 2004/0098033 A1 | 5/2004 | Leeflang et al. |
| 2003/0150821 A1 | 8/2003 | Bates et al. | 2004/0102806 A1 | 5/2004 | Broome et al. |
| 2003/0153935 A1 | 8/2003 | Mialhe | 2004/0102807 A1 | 5/2004 | Kusleika et al. |
| 2003/0153942 A1 | 8/2003 | Wang et al. | 2004/0106944 A1 | 6/2004 | Daniel et al. |
| 2003/0153943 A1 | 8/2003 | Michael et al. | 2004/0111111 A1 | 6/2004 | Lin |

| Publication No. | Date | Inventor |
|---|---|---|
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salahieh et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225321 A1 | 11/2004 | Krolik et al. |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Streeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salahieh et al. |
| 2006/0015138 A1 | 1/2006 | Gertner et al. |
| 2006/0015139 A1 | 1/2006 | Tsugita et al. |
| 2006/0015140 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |

| | | |
|---|---|---|
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0 472 334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/45592 | 6/2001 |
| WO | WO01/87183 | 11/2001 |

* cited by examiner

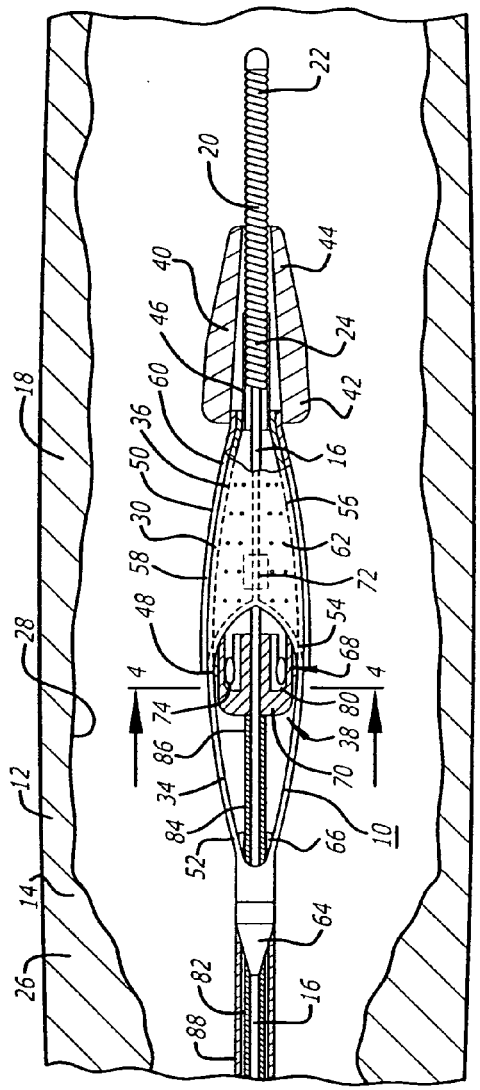
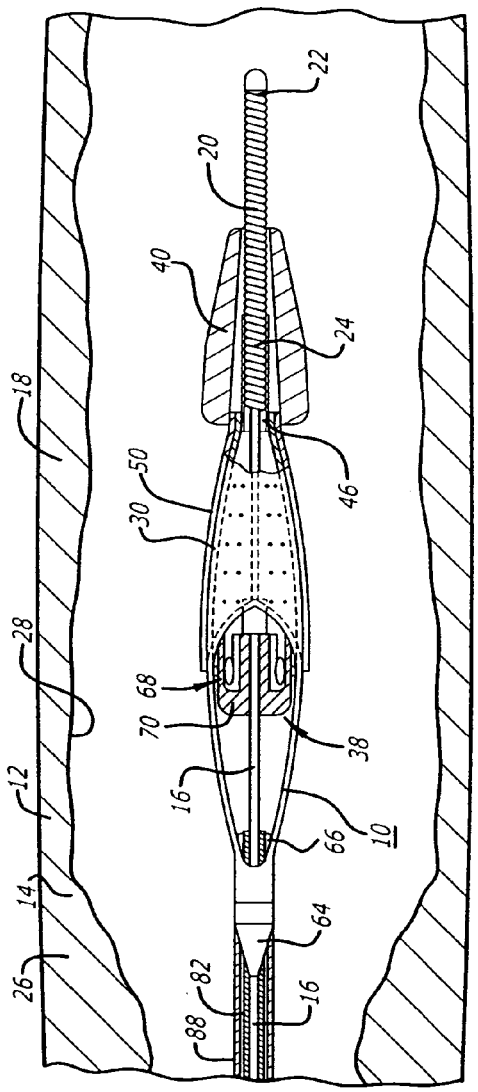
FIG. 1
FIG. 2

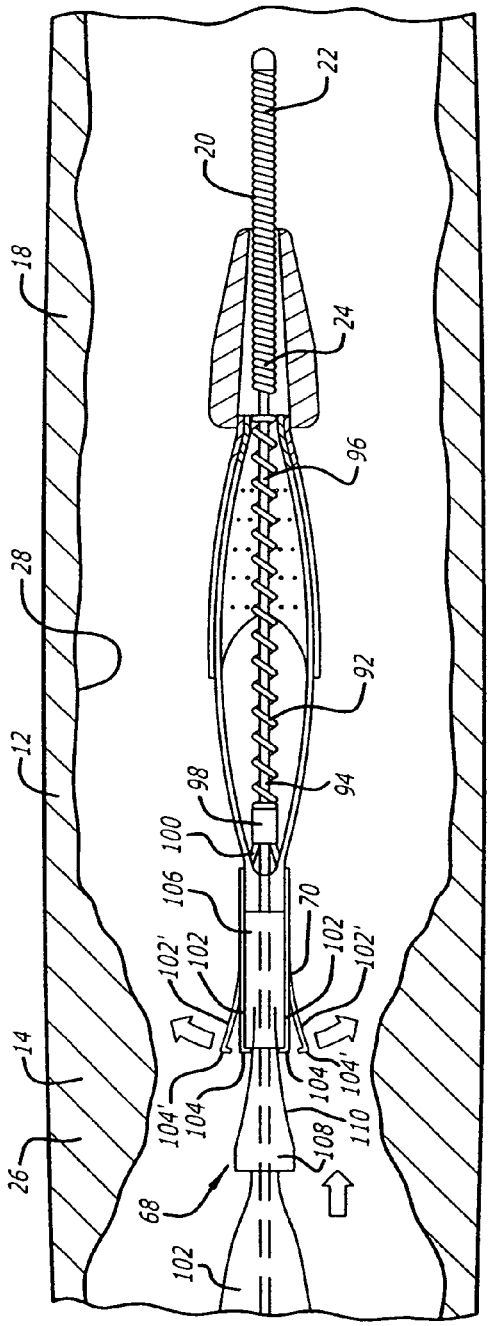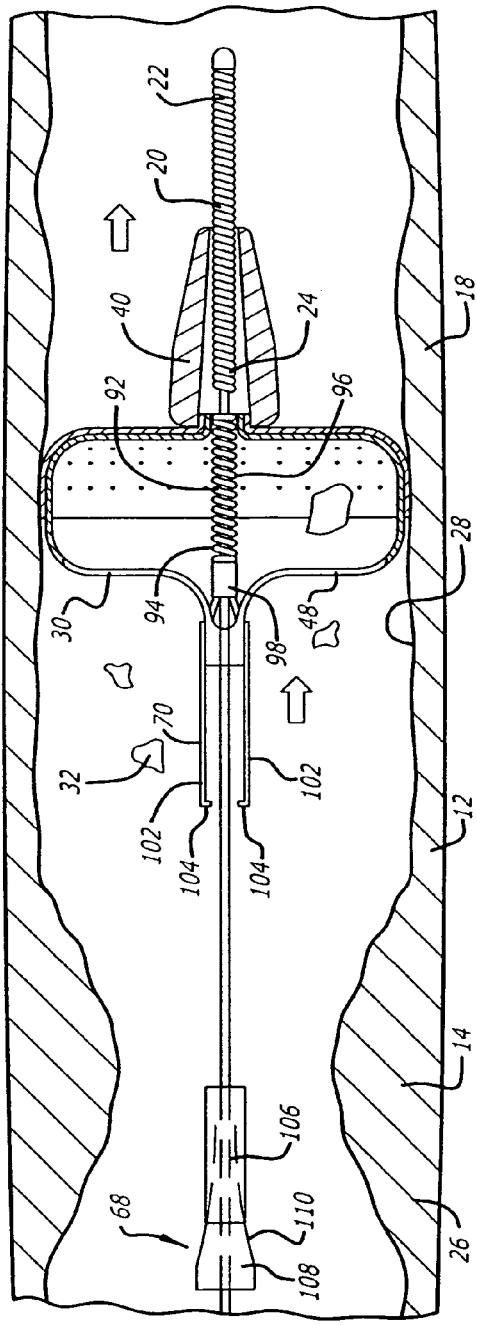

SHEATHLESS EMBOLIC PROTECTION SYSTEM

RELATED APPLICATIONS

This Application is a continuation application of U.S. Ser. No. 09/945,152 filed Aug. 31, 2001, now U.S. Pat. No. 7,018, 393, which is a continuation-in-part application of application Ser. No. 09/740,560 filed Dec. 19, 2000, which is now U.S. Pat. No. 6,506,203.

BACKGROUND OF THE INVENTION

The present invention relates generally to improvements in embolic protection systems and methods. In particular, it relates to an improved system and method for enabling an embolic protection device to be efficiently and conveniently compressed and retained in compressed condition so as to cross a stenosis in a low profile and be delivered through the patient's vasculature to a location distal to the site of an interventional procedure, without a sheath extending about the filter device. The system also enables the device to be effectively released from compression thereof at the location distal to the interventional procedure site, for enabling expansion and deployment of the filter device for capturing embolic material.

The systems and methods of the present invention are particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of an embolic protection device such as a filter or trap downstream from the treatment site to capture embolic debris before it reaches the smaller blood vessels downstream. Such embolic protection devices enable the filtering of embolic debris which may be released into the bloodstream during the treatment to the vessel, and yet allow a sufficient amount of oxygenated blood to flow past the device to supply vital organs downstream from the treatment site.

However, there have been problems associated with filtering systems, particularly during the insertion, expansion, deployment, and removal of the filter within the blood vessel. The filter needs to cross the stenosis in as small a profile as possible so as to clear the stenosis and prevent damage thereto. Previous designs have employed an outer catheter called a "sheath" to keep these filters constrained prior to delivery beyond the stenosis. This outer catheter necessarily increases the profile of the device which could in and of itself create embolic complications as this high profile device is forced through the stenosis. After crossing the stenosis and being positioned distal to the interventional procedure site, the filter needs to be deployed, and after the interventional procedure has been performed, the filter needs to be removed with the captured embolic material therein, in an efficient and effective manner.

Therefore, the present invention provides improved systems and methods for treating stenosis in blood vessels which reduces the profile and improves the stenosis crossing characteristics of a filter, for crossing the stenosis to a position distal to the interventional procedure site for deployment of the filter. It also enables effective filter deployment at the position distal to the interventional procedure site, and removal from the position distal to the interventional procedure site, for capturing embolic debris in the bloodstream that can cause blockage in vessels at downstream locations. The improved systems and methods of the present invention further enable filtering of embolic debris which may be released into the bloodstream during the treatment to the vessel, and allow a sufficient amount of oxygenated blood to flow past the filtering device to supply vital organs downstream from the treatment site. Moreover, the systems and methods are relatively easy for a physician to use, while enabling the effective delivery and recover of a filtering system capable of removing embolic debris released into the bloodstream. The inventions disclosed herein satisfy these and other needs.

SUMMARY OF THE INVENTION

The present invention, in general, provides a system and method for enabling the insertion and removal of a filtering system for capturing and retaining embolic debris from a blood vessel. The embolic debris may be created during the performance of a therapeutic interventional procedure, such as a balloon angioplasty or stenting procedure. The filtering system prevents the embolic debris from lodging and blocking blood vessels downstream from the interventional site. The present invention is particularly useful for enabling an interventional procedure to be performed in vital arteries, such as the carotid arteries, in which critical downstream blood vessels can become blocked with embolic debris, including the main blood vessels leading to the brain or other vital organs. As a result, the present invention provides the physician with a higher degree of confidence in the efficient operation of a filtering system for the collection and removal of embolic debris from the blood vessel when performing high-risk interventional procedures.

The present invention enables a filtering system to be deployed in the blood vessel at a location distal to the area of treatment in the interventional procedure site. It also enables the blood to pass therethrough to enable blood to flow past the filter. It further enables the blood to be filtered to capture and retain any embolic debris which may be created during the interventional procedure.

More particularly, for example, in an embodiment of the present invention, a system is provided for enabling the capture of embolic material which may be released into a blood vessel during a therapeutic interventional procedure at a site of a stenosis. The present invention also enables the system to expand against the inner surface of a wall of a blood vessel so as to efficiently seal off the inner surface thereof, for enabling the capture of embolic material which may be released into the blood vessel during the therapeutic interventional procedure. Further, the system enables navigation thereof through a patient's blood vessel, including tortuous vasculature, to a position distal to an interventional procedure site, for deployment of the embolic protection device.

The system includes a guide wire, including a distal end, which is positionable within the blood vessel so as to extend to a position distal to an interventional procedure site. The system also includes a filter device, which is positionable and able to be deployed at a location in the patient's vasculature distal to the interventional procedure site, and to capture embolic material which may be released into the blood in the blood vessel during the interventional procedure. The system further includes a compressing element, for compressing the filter device so as to enable the filter device to be inserted over the guide wire, to the position distal to the interventional procedure site, in a low profile for crossing the stenosis, and without a sheath extending about the filter device. The filter device also enables the release of the compressing element, so as to enable expansion of the filter device for deployment thereof.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 1 is an elevational fragmentary partly-sectional view of a first version of a first embodiment of the present invention, disposed within the internal carotid artery of a patient, including a filter device which is compressed and retained in compression by an inner tube extending therein.

FIG. 2 is a similar view of the first version of the first embodiment shown in FIG. 1, wherein the filter device is compressed and is not retained in compression by the inner tube therein.

FIG. 9 is an elevational fragmentary partly-sectional view of a second embodiment of the present invention, disposed within the internal carotid artery of a patient, including a filter device which is compressed and retained in compression.

FIG. 10 is a similar view of the second embodiment in FIG. 9, wherein compression of the filter device has been released and the filter device has expanded.

DETAILED DESCRIPTION OF THE PREFERRED EMBODIMENTS

Figure 3:
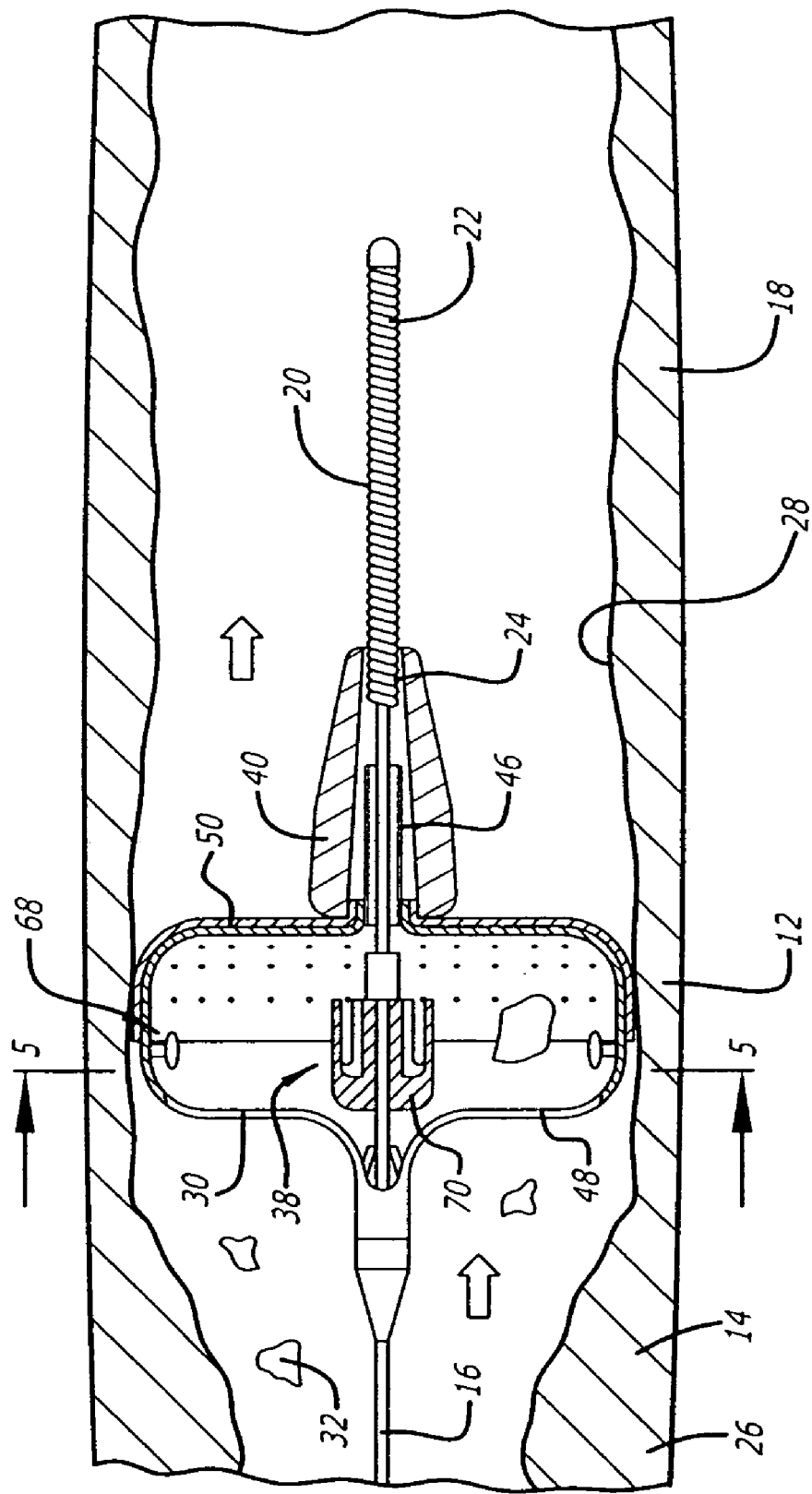
FIG. 3 is a similar view of the first version of the first embodiment shown in FIG. 1, wherein compression of the filter device has been released and the filter device has expanded.

The present invention is directed to an improved system and method for enabling the capture of embolic material which may be released into the blood vessel during a therapeutic interventional procedure, in an efficient and effective manner. The invention enables a filter device to be compressed, for efficient insertion thereof through the patient's vasculature so as to cross a stenosis in a low profile at the site of the interventional procedure, without a sheath extending about the filter device. The present invention is further directed to effectively enabling the release of compression thereof, for expansion and deployment of the filter device at a location distal to the interventional procedure site.

The embodiments of the improved system and method are illustrated and described herein by way of example only and not by way of limitation. While the present invention is described as applied to the carotid arteries of the patient, those skilled in the art will appreciate that it can also be used in other body lumens as well, such as the coronary arteries, renal arteries, saphenous vein grafts and other peripheral arteries. Additionally, the present invention can be utilized when performing any one of a number of interventional procedures, such as stenting, balloon angioplasty, laser angioplasty or atherectomy.

In the drawings, wherein like reference numerals denote like or corresponding parts throughout the drawing figures, and particularly in the embodiments in accordance with the invention as shown in FIGS. 1-10, for example, a system 10 is provided for enabling an interventional procedure to be performed in a blood vessel 12 at an area of treatment 14. The system 10 is atraumatic, to inhibit injury to the patient. It includes a guide wire 16 which enables the system 10 to be positioned distal to the area of treatment 14. The system 10 is placed within the carotid artery 18 or other blood vessel of the patient, and is guided into position by the guide wire 16. The guide wire 16 includes a tip coil 20 at a distal end 22 thereof. The tip coil includes a proximal end 24. The tip coil 20 is attached at the proximal end thereof to the guide wire 16 for example by solder. The carotid artery 18 has the area of treatment 14 therein, which comprises the interventional procedure site, wherein atherosclerotic plaque 26 has built up against the inside wall 28, which decreases the diameter of the carotid artery 18. As a result, blood flow is diminished through this area.

The therapeutic interventional procedure comprises implanting an expandable interventional instrument at the interventional procedure site 14, to press the build-up of plaque 26 of the stenosis against the inside wall 28, to increase the diameter of the occluded area 14 of the artery 18, and to help restore sufficient flow of blood to the downstream vessels leading to the brain. The expandable interventional instrument not only helps increase the diameter of the occluded area, but helps prevent restenosis in the area of treatment 14. The interventional instrument is expandable upon deployment thereof at the interventional procedure site 14.

The system 10 of the present invention enables the delivery of a filter device 30 to a location distal to the area of treatment 14, to enable deployment of the filter device 30 at the location distal to the area of treatment 14, and to enable the removal of the filter device 30 from the delivered and deployed position thereof. The filter device 30 filters the blood in the blood vessel 12, so as to pass blood therethrough and capture embolic material 32 which may be released in the blood vessel 12 during the interventional procedure. It is secured to the distal end 22 of the guide wire 16, so as to enable the filter device 30 to be placed within the carotid artery 18 or other blood vessel of the patient and guided into position distal to the area of treatment 14. The filter device 30 includes a proximal portion 34 and a distal portion 36.

Referring to FIGS. 1-10, in embodiments pursuant to the present invention, for example, the system 10 enables compressed low profile movement thereof without a sheath, through the patient's blood vessel 12, to a position distal to the area of treatment 14 for deployment of the filter device 30. The system 10 further enables the release of the compression thereof, for expansion of the filter device 30 against the inside wall 28 of the blood vessel 12 and the sealing off of the inside wall 28, to enable the capture of embolic material 32 which may be released into the blood vessel 12 during the therapeutic interventional procedure.

The system 10 includes the guide wire 16, positionable within the blood vessel 12, and extendable to a position distal to the interventional procedure site 14. The system 10 further includes the filter device 30, which includes a compressing element 38 for compression thereof, to enable the filter device 30 to be compressed in a low profile at the distal end 22 of the guide wire 16, and to be retained in compressed condition, for delivery thereof to the position distal to the interventional procedure site 14, without a sheath extending about the filter device 30. The compressing element 38 is releasable from compressing the filter device 30 at the location distal to the interventional procedure site 14, to enable expansion of the filter device 30 for deployment thereof.

The system 10 further includes an obturator 40, which includes a proximal end 42 and a distal end 44. The obturator 40 extends between the distal portion 36 of the filter device 30 and the tip coil 20. The obturator 40 provides a smooth transition between the distal portion 36 of the filter device 30 and the tip coil 20, so as to enable the distal portion 36 of the filter device 30 to slide smoothly around tortuous anatomy in the blood vessel 12, and to inhibit digging into, scraping, or damaging the inside wall 28 of the blood vessel 12 thereby. The distal portion 36 of the filter device 30 further includes a tube 46, comprised for example of polyimide material, for enabling the obturator 40 to be bonded and assembled thereover.

The filter device 30 further includes a cage 48, which is engageable with the distal end 22 of the guide wire 16, and filter material 50, for filtering embolic material 32, which is secured to the cage 40. The cage 48 includes a proximal portion 52, a medial portion 54, and a distal portion 56. The filter material 50 includes a proximal end 58, a distal end 60, and a plurality of holes 62 therein for filtering embolic material 32. The proximal end 58 of the filter material 50 is secured to the medial portion 54 of the cage 48, and the proximal end 42 of the obturator 40 extends over the distal end 60 of the filter material 50. The proximal portion 52 of the cage 48 includes a channel 64 extending therethrough, and at least one tab 66. The tabs 66 are extendable in the distal direction, and are pre-bent so as to be extendable radially towards the guide wire 16.

The compressing element 38 includes an engageable element 68, engageable with the filter device 30 so as to enable compression of the filter device 30. It further includes an engaging element 70, for engaging the engageable element 68 so as to retain compression of the filter device 30, and for releasing from engagement with the engageable element 68 to enable the release of compression of the filter device 30 for expansion and deployment thereof.

Figure 4:
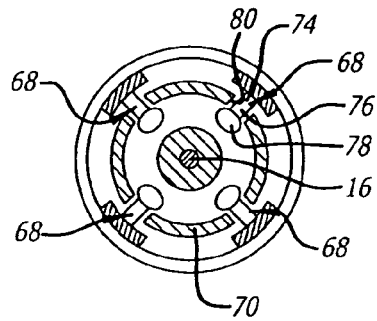
FIG. 4 is a cross-sectional view taken along the line 4-4 of FIG. 1.
Figure 5:
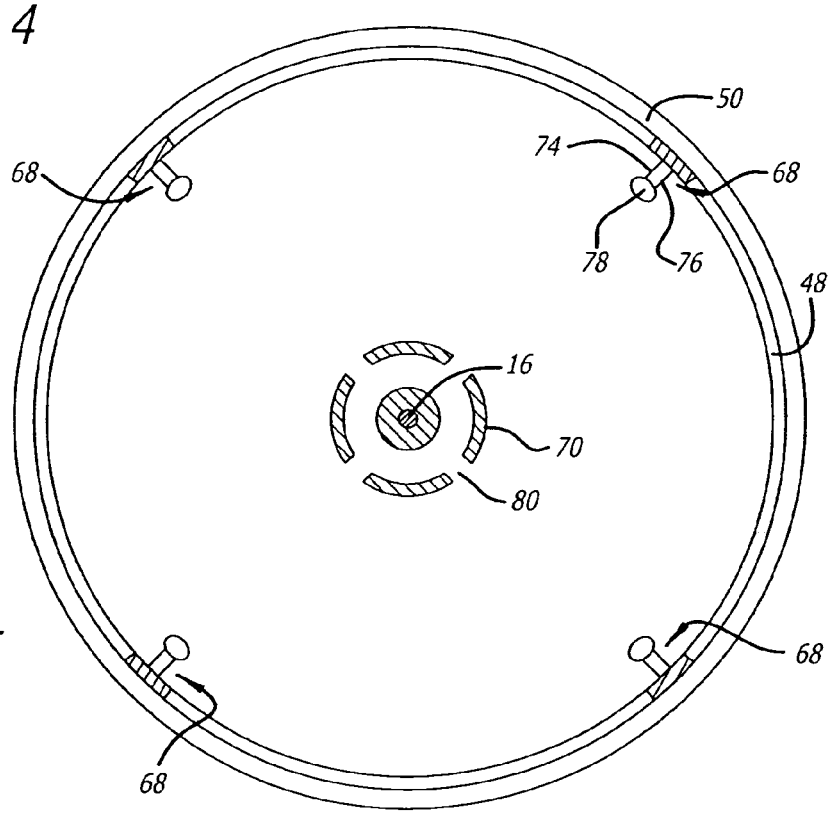
FIG. 5 is a cross-sectional view taken along the line 5-5 of FIG. 3.

In a first version of a first embodiment pursuant to the present invention, as shown in FIGS. 1-5, a stop member 72 is secured to the distal end 22 of the guide wire 16, spaced proximal of the proximal end 24 of the tip coil 20. The stop member 72 may for example comprise a tapered stop which includes a radiopaque marker band thereon, for providing a reference for positioning the filter device 30 in the patient's vasculature 12. The engageable element 68 of the compressing element 38 comprises at least one tab member 74, projecting generally radially inwardly from the outer surface of the cage 48 of the filter device 30. The tab members 74 each include a relatively narrow projecting portion 76, and a relatively enlarged end portion 78. There may for example be four tab members, spaced ninety-degrees apart about the cage 40, as seen in FIGS. 3 and 4. The engaging element 70 for example is generally ring-shaped, and includes at least one slot 80 therein extending and opening in a generally distal direction therein. The tab members 74 of the engageable element 68 are engageable with and releaseable from the slots 80 in the engaging element 70.

The system 10 further includes a delivery enabling element 82, which bears against the compressed filter device 30 for enabling delivery thereof to the position distal to the interventional procedure site 14, without extending about the filter device 30. The delivery enabling element 82 is also able to be withdrawn from bearing against the filter device 30. The delivery enabling element 82 includes an inner tube 84, which is extendable about the guide wire 16, and which includes a distal end 86 which is extendable into the filter device 30, through the channel 64 in the proximal portion 34 thereof, so as to bear against the compressing element 38. The inner tube 84 also pushes the tab members 74 radially outwardly and into engagement therewith upon extending through the channel 64. The delivery enabling element 82 also includes an outer tube 88, extendable about the inner tube 84, which bears against the proximal portion 34 of the filter device 30 for delivery thereof.

Figure 8:
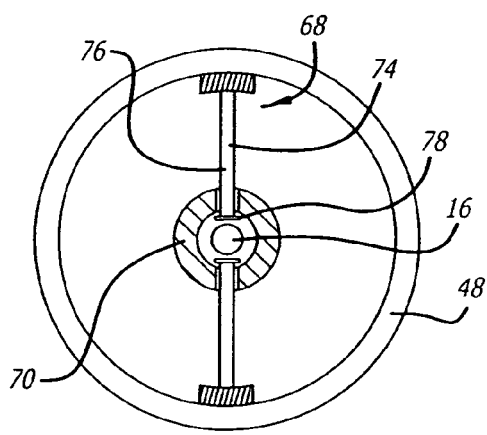
FIG. 8 is a cross-sectional view taken along the line 8-8 of FIG. 6.
Figure 6:
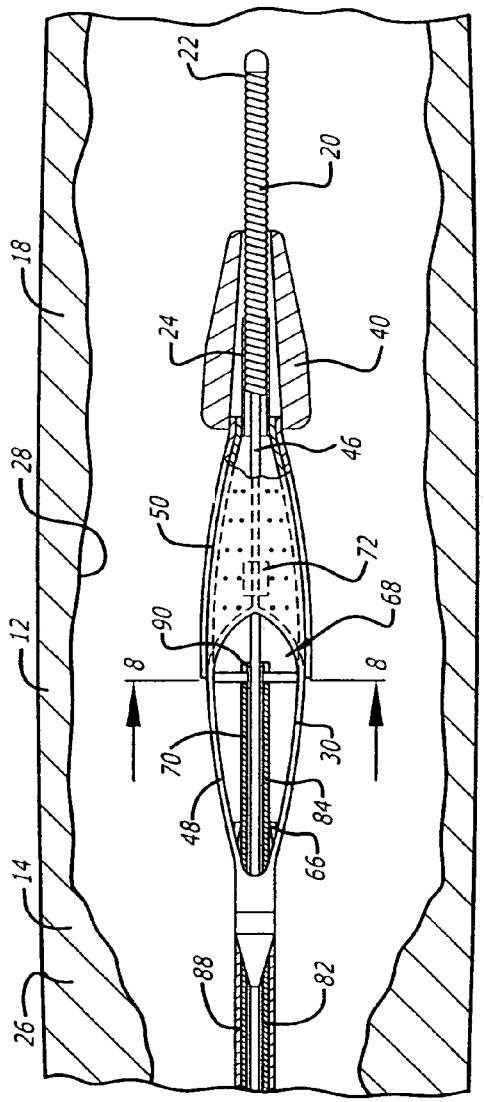
FIG. 6 is an elevational fragmentary partly-sectional view of a second version of the first embodiment of the present invention, disposed within the internal carotid artery of a patient, including a filter device which is compressed and retained in compression by an inner tube extending therein.
Figure 7:
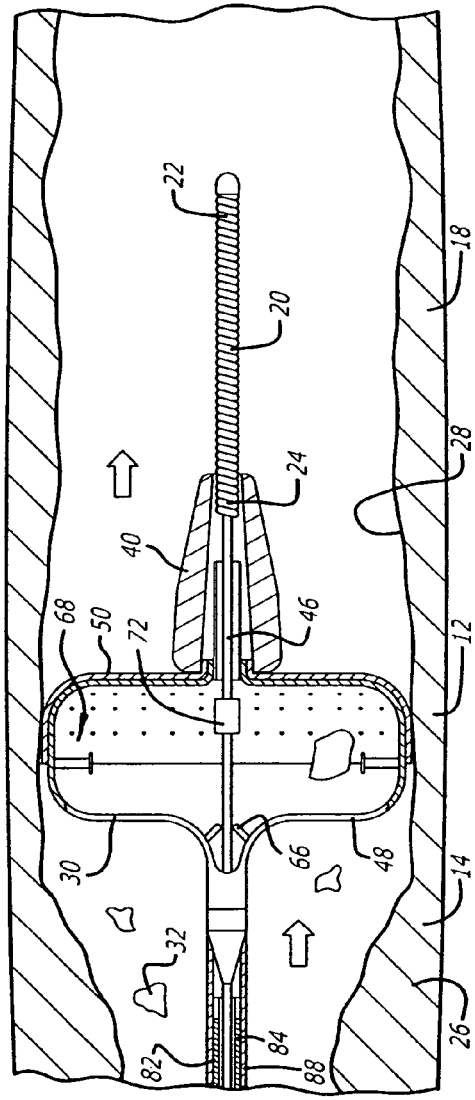
FIG. 7 is a similar view of the second version of the first embodiment in FIG. 6, wherein compression of the filter device has been released and the filter device has expanded.

As shown in FIGS. 6-8, in a second version of the first embodiment, the inner tube 84 comprises the engaging element 70, and includes at least one slot 90 in the distal end 86 thereof, which opens in the distal direction, for receiving the tab member 74 of the engageable element 68 therein.

In a second embodiment of the invention, as illustrated in FIGS. 9-10, the filter device 30 further includes a normally-compressed member 92, which is expandable and retained in the expanded condition by the compressing element 38 for compression of the filter device 30. The normally-compressed member 92 is biased to compress upon release of the compressing element 38, to release the compressed filter device 30 for expansion and deployment of the filter device 30. The normally-compressed member 92 includes a proximal end 94 and a distal end 96. The normally-compressed member 92 for example comprises a spring.

The filter device 30 further includes a stop 98 in the proximal portion 34 thereof, and a space 100 between the proximal portion 52 of the cage 40 and the stop 98 into which the tabs 66 are extendable to bear against the stop 98. The proximal end 94 of the spring 92 bears against the stop 98. The filter device 30 also includes an engaging member 102, engageable with the engageable element 68, and releaseable therefrom responsive to engagement of the engaging element 70 with the engageable element 68. The engaging member 102 comprises at least one strut, including a proximal tip portion 104, positionable so as to extend radially inwardly towards the guide wire 16.

The engageable element 68 includes a distal section 106, secured to the guide wire 16, substantially uniform in diameter, which is engageable by the engaging element 70. It further includes a proximal section 108, movable relative to the distal section 106, so as to release the struts 102 of the filter device 30 from engagement with the engageable element 68. The proximal section 108 of the engageable element 68 includes a portion 110, the diameter of which increases in the proximal direction, which guides the struts 102 of the filter device 30 therealong so as to expand radially outwardly upon movement of the proximal section 108 in the distal direction relative to the distal section 106, until the struts 102 release from engagement with the distal portion 106 of the engageable element 68. The engaging element 70 comprises for example a balloon catheter.

Referring to FIGS. 1-10, in a method for the use of the embodiment in accordance with the present invention, for example, the system 10 enables delivery thereof in a low profile through the patient's blood vessel 12 to the location distal to the area of treatment 14 for deployment of the filter device 30, and seals off the inside wall 28 of the blood vessel 12 to enable the capture of embolic material 32. The filter device 30 is compressed by engaging the engaging element 70 with the engageable element 68 of the compressing element 38, so as to engage the compressing element 38 with the filter device 30. The compressed filter device 30 is engaged with the distal end 22 of the guide wire 16. The compressed filter device 30 is then delivered with the guide wire 16 in the low profile, for crossing the stenosis 14, without a sheath extending thereabout, to the location in the patient's vasculature 12 distal to the interventional procedure site 14. The compressing element 38 is then released, by releasing the engaging element 70 from engaging the engageable element 68, so as to enable the filter device 30 to expand and deploy, to capture embolic material 32 which may be released during the interventional procedure.

The delivery enabling element 82, in the first embodiment of the invention as seen in FIGS. 1-6, bears against the compressed filter device 30 for enabling delivery thereof to the position distal to the interventional procedure site 14, without extending about the filter device 30. The delivery enabling element 82 is withdrawn from bearing against the filter device 30, for enabling release of the compressed filter device 30 for expansion and deployment thereof at the position distal to the interventional procedure site 14.

In the first version of the first embodiment of the present invention, as shown in FIGS. 1-5, the slots 80 in the engaging element 70 are engaged with the tab members 74 of the engageable element 68, to compress the filter device 30. An assembly of the compressed filter device 30 is inserted for example over the proximal end of the guide wire 16 extending outside the patient. The compressed filter device 30 is advanced over the proximal end of the guide wire 16 into the patient's body and onto the distal end 22 of the guide wire 16. The distal end 86 of the inner tube 84 of the delivery enabling element 82 is extended through the channel 64 in the proximal portion 34 of the filter device 30 so as to bear against the engaging element 70, to retain the filter device 30 in the compressed condition thereof. The outer tube 88 of the delivery enabling element 82 bears against the proximal portion 34 of the filter device 30 for enabling delivery of the filter device 30 to the location for deployment thereof. Delivery systems may be configured in over the wire or rapid exchange delivery platforms.

Upon reaching the location distal to the interventional procedure site 14, the distal end 86 of the inner tube 84 is pulled in the proximal direction away from its position bearing against the engaging element 70, to a position for example extending slightly distal of the tabs 66, leaving a space between the distal end 86 of the inner tube 84 and the engaging element 70. The guide wire 16 is then pulled in the proximal direction, pulling the stop member 72 into engagement with the engaging element 70. Upon pulling the guide wire 16 further in the proximal direction, the tab members 74 of the engageable element 68 slide out of the slot 80 in the engaging member 70, releasing the tab members 74 from the slots 80 so as to enable expansion and deployment of the filter device 30. Alternatively, for example, a slightly larger tip coil 20 may be used to push the engaging element 70 and deploy the filter device 30.

The slots 90 of the inner tube 84, in the second version of the first embodiment of the invention, as depicted in FIGS. 6-8, engage the tab members 94 of the engageable element 68, to compress the filter device 30, and to retain the filter device 30 in the compressed condition during delivery. The outer tube 88 bears against the proximal portion 34 of the filter device 30 for enabling delivery of the filter device to the deployment location thereof. The distal end 86 of the inner tube 84 is pulled in the proximal direction, away from engagement with the engageable element 68, upon reaching the position distal to the interventional procedure site 14, for releasing the tab members 74 from the slots 80, and the tabs 66 engage the guide wire 16, for enabling expansion and deployment of the filter device 30.

As illustrated in FIGS. 9-10, in the second embodiment of the present invention, an assembly of the filter device 30 and the obturator 40 is inserted for example over the proximal end of the guide wire 16 up to the position where the tabs 66 snap-fit into the space 100 so as to bear against the stop 98. The spring 92 is expanded, and the struts 102 of the filter device 30 engage the distal section 106 of the engageable element 68. The guide wire 16 is then pushed through the patient's vasculature 12, with the filter device 30 in compressed low profile condition, until the distal end 22 of the guide wire 16 reaches the position distal to the interventional procedure site 14. The balloon catheter 70 is then inserted over the guide wire 16 and through the patient's vasculature 14 until it engages the proximal section 108 of the engageable element 68. Upon pushing the balloon catheter 70 further in the distal direction, the proximal section 108 of the engageable element 68 moves distally into the distal section 106 thereof which is secured to the guide wire 16, causing the struts 102 of the filter device 30 to move radially outwardly along the guiding portion 110 of the proximal section 108. Upon sufficient radially-outward movement of the struts 102 along the guiding surface 110 of the proximal section 108 of the engageable element 68, the struts release from engagement with the distal section 106, releasing the filter device 30 from engagement therewith, and enabling the spring 92 to compress, resulting in expansion and deployment of the filter device 30 for capturing embolic material 32.

In accordance with the present invention, the particular embodiments set forth above of the system 10 for filtering embolic material are capable of being positioned in a blood vessel. However, other forms of the system 10 may be utilized with the present invention without departing from the spirit and scope of the invention. For example, the system 10 may be comprised of other forms of material. Additionally, while the system 10 is shown in various shapes in the embodiments herein, it can be formed in any one of a number of different shapes depending upon the construction desired.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed. Based on the present disclosure, other adhesives and applications are known to one skilled in the art.

In view of the above, it is apparent that the system and method of the embodiment of the present invention enhances substantially the effectiveness of performing interventional procedures by providing a filter device for filtering embolic material, to be compressed in a low profile for crossing a stenosis without a sheath extending about the filter device, and to be retained in compressed condition thereof, for delivery to a position distal to an interventional procedure site. The system and method further enable release of compression of the filter device at the location distal to the area of treatment of the stenosis, enabling the filter device to expand and deploy so as to capture embolic material.

While the present invention has been described in connection with the specific embodiments identified herein, it will be apparent to those skilled in the art that many alternatives, modifications and variations are possible in light of the above description. Accordingly, the invention is intended to embrace all such alternatives, modifications and variations as may fall within the spirit and scope of the invention disclosed herein.

What is claimed:

1. A system for capturing embolic material in a body vessel, comprising:
   a guide wire;
   a filter device on the guide wire, the filter device having an interior including an engageable element and an exterior and being movable between a compressed delivery position and a deployed position;
   a compressing element located in the interior of the filter device for maintaining the filter device in the compressed delivery position, the compressing element including a slot which receives the engageable element and is removably connected to the filter device and adapted to disengage from the filter device to move the filter device into the deployed position; and
   a delivery enabling element adapted to disengage the compressing element from its connection with the engageable element of the filter device to allow the filter device to move into the deployed position.

2. A system for capturing embolic material in a body vessel, comprising:
   a guide wire;
   a filter device on the guide wire, the filter device having an interior including an engageable element and an exterior and being movable between a compressed delivery position and a deployed position;
   a compressing element located in the interior of the filter device for maintaining the filter device in the compressed delivery position, the compressing element having a structure which receives the engageable element so that the compressing element is removably connected to the filter device and adapted to disengage from the filter device to move the filter device into the deployed position; and a delivery enabling element coupled to the filter device and adapted to disengage the compressing element from its connection with the filter device to move the filter device into the deployed position, wherein the filter device is slidably disposed on the guide wire and the delivery enabling element is adapted to move the filter device along the length of the guide wire.

3. The system of claim 2, wherein the delivery enabling element is removably coupled to the filter device.

4. The system of claim 2, wherein the filter device includes a locking mechanism for locking the filter device to the guide wire.

5. The system of claim 4, wherein the delivery enabling element maintains the locking mechanism in an unlocked position and is adapted to move the locking mechanism into a locked position on the guide wire.

6. The system of claim 5, wherein the locking mechanism is a deflectable tab.

7. The system of claim 2, wherein the delivery enabling element has a distal end coupled to the filter device and a proximal portion which can be manipulated to disengage the compressing element from its connection with the filter device.

8. The system of claim 2, wherein the delivery enabling element includes an outer member co-axially disposed over an inner member, the inner member being in contact with the compressing element to maintain the compressing element connected to the filter device to maintain the filter device in the compressed position.

9. The system of claim 8, wherein the filter device includes a locking mechanism for locking the filter device to the guide wire and the inner member of the delivery enabling element maintains the locking mechanism in an unlocked position and is adapted to move the locking mechanism into a locked position on the guide wire.

10. The system of claim 8, wherein the inner member of the delivery enabling element includes a lumen for receiving the guide wire.

11. The system of claim 2, wherein the delivery enabling element includes a lumen for receiving the guide wire.

12. The system of claim 2, wherein the filter device includes a self-expanding cage and a filter element attached to the self-expanding cage.

13. The system of claim 2, wherein the compressing element remains within the interior of the filter device after the filter device is placed in the deployed position.

14. The system of claim 13, wherein the compressing element is integral with the delivery enabling element.

15. The system of claim 2, wherein the guide wire includes a stop member mounted thereto which abuts against the compressing element to allow the compressing element to disengage from the filter device.

16. A system for capturing embolic material in a body vessel, comprising:
a guide wire;
a filter device on the guide wire, the filter device having an interior and an exterior and being movable between a compressed delivery position and a deployed position;
a compressing element located in the interior of the filter device for maintaining the filter device in the compressed delivery position, the compressing element being removably connected to the filter device and adapted to disengage from the filter device to move the filter device into the deployed position; and
a delivery enabling element coupled to the filter device and adapted to disengage the compressing element from its connection with the filter device to move the filter device into the deployed position, wherein the filter device is slidably disposed on the guide wire and the delivery enabling element is adapted to move the filter device along the length of the guide wire,
wherein the delivery enabling element includes an outer member co-axially disposed over an inner member, the inner member being in contact with the compressing element to maintain the compressing element connected to the filter device to maintain the filter device in the compressed position and the contact between the inner member and compressing element is removed to allow the filter device to move into the deployed position.

17. A method for capturing embolic material which may be released into a body vessel during an interventional procedure by using a system including a filter device having an interior including an engageable element and an exterior and a compressing element located in the interior of the filter device for compressing and maintaining the device in a compressed delivery position, the compressing element having a structure which receives the engageable element so that the compressing element is removably connected to filter device and adapted to disengage from the filter device to move the filter device into a deployed position and a delivery enabling element coupled to the filter device and adapted to disengage the compressing element from its connection with the filter device to move the filter device into the deployed position, the method comprising:
compressing a filter device by engaging the compressing element with the engageable element located in the interior of the filter device;
advancing a guide wire into a region of interest within the body vessel;
delivering the compressed filter device by moving it along the length of the guide wire using the delivery enabling element to the location in the patient's vasculature distal to the interventional procedure site; and
releasing the connection between the compressing element and the engageable element to move the filter device into the deployed position.

18. The method of claim 17, further including:
removing the delivery enabling element from the filter device;
advancing an interventional device over the guide wire to the interventional procedure site;
performing the interventional procedure wherein any released embolic debris is captured by the filter device;
removing the interventional device from the interventional procedure site; and
removing the filter device from the body vessel.

19. A method for capturing embolic material which may be released into a body vessel during an interventional procedure by using a system including a filter device having an interior including at least one engageable element and an exterior and a compressing element located in the interior of the filter device for maintaining the device in a compressed delivery position, the compressing element having at least one slot which is removably connected to the at least one engageable element of the filter device and adapted to disengage from the at least one engageable element of filter device to move the filter device into a deployed position and a delivery enabling element coupled to the filter device and adapted to disengage the compressing element from its connection with the at least one engageable element of filter device to move the filter device into the deployed position, the method comprising:
compressing the filter device by engaging the compressing element with the filter device;

advancing the guide wire and filter device into a region of interest within the body vessel; and releasing the connection between the slot of the compressing element and at least one engageable element of filter device to move the filter device into the deployed position.

20. The method of claim 19, further including:

removing the delivery enabling element from the filter device;

advancing an interventional device over the guide wire to the interventional procedure site;

performing the interventional procedure wherein any released embolic debris is captured by the filter device;

removing the interventional device from the interventional procedure site; and removing the filter device from the body vessel.

21. The method of claim 20, further including:

locking the filter device on the guide wire after the filter device has been advanced into the region of interest in the body vessel.

* * * * *

UNITED STATES PATENT AND TRADEMARK OFFICE
CERTIFICATE OF CORRECTION

| | | |
|---|---|---|
| PATENT NO. | : 7,662,166 B2 | Page 1 of 1 |
| APPLICATION NO. | : 11/352713 | |
| DATED | : February 16, 2010 | |
| INVENTOR(S) | : William J. Boyle et al. | |

It is certified that error appears in the above-identified patent and that said Letters Patent is hereby corrected as shown below:

Column 6, line 56, delete "40" and insert instead --48--.

Column 7, lines 22 and 64, delete "40" and insert instead --48--.

Column 12, line 21, after "to" insert --the--.

Signed and Sealed this
Eighth Day of February, 2011

David J. Kappos
*Director of the United States Patent and Trademark Office*